(12) United States Patent
Wang

(10) Patent No.: US 7,089,121 B1
(45) Date of Patent: Aug. 8, 2006

(54) METHODS FOR MONITORING THE EXPRESSION OF ALTERNATIVELY SPLICED GENES

(75) Inventor: Hui Wang, San Mateo, CA (US)

(73) Assignee: Affymetrix, Inc., Santa Clara, CA (US)

( * ) Notice: Subject to any disclaimer, the term of this patent is extended or adjusted under 35 U.S.C. 154(b) by 0 days.

(21) Appl. No.: 10/448,566

(22) Filed: May 29, 2003

Related U.S. Application Data

(63) Continuation of application No. 10/384,275, filed on Mar. 6, 2003, now abandoned.

(60) Provisional application No. 60/433,135, filed on Dec. 13, 2002, provisional application No. 60/422,220, filed on Oct. 29, 2002, provisional application No. 60/398,958, filed on Jul. 26, 2002, provisional application No. 60/384,552, filed on May 30, 2002, provisional application No. 60/433,225, filed on Dec. 13, 2002.

(51) Int. Cl.
 *G06F 19/00* (2006.01)
 *G06F 17/00* (2006.01)
(52) U.S. Cl. ............................. 702/20; 702/19; 435/6
(58) Field of Classification Search .................. 702/19, 702/20; 435/6
 See application file for complete search history.

(56) References Cited

OTHER PUBLICATIONS

Gelfand et al (Proc. Natl. Acad. Sci. USA 93: 9061 (1996)).*
Mironov et al (Genomics 51: 332 (1998)).*
Flores et al (Genome Res. 8: 967 (1998)).*
Wang et al., "Gene Structure-Based Splice Variant Deconvolution Using a Microarray Platform", Bioinformatics (2003) vol. 18 Suppl. 1: 1315-1322.
Li and Wong, "Model-Based Analysis of Oligonucleolide Arrays: Expression Index Computation and Outlier Detection", Proc. Natl. Acad. Sci. (2001) vol. 98 No. 1: 31-36.
Hu et al., "Predicting Splice Variant from DNA Chip Expression Data", Genome Research (2001) 11: 1237-1245.

* cited by examiner

*Primary Examiner*—James Martinell
(74) *Attorney, Agent, or Firm*—Affymetrix, Inc.

(57) ABSTRACT

Methods, probe arrays and computer software products are provided for determining the arrangement of sequence elements. In one embodiment, methods for making and using exon chips are provided. The exon chips may be used to identify and quantify splice variants.

7 Claims, 6 Drawing Sheets

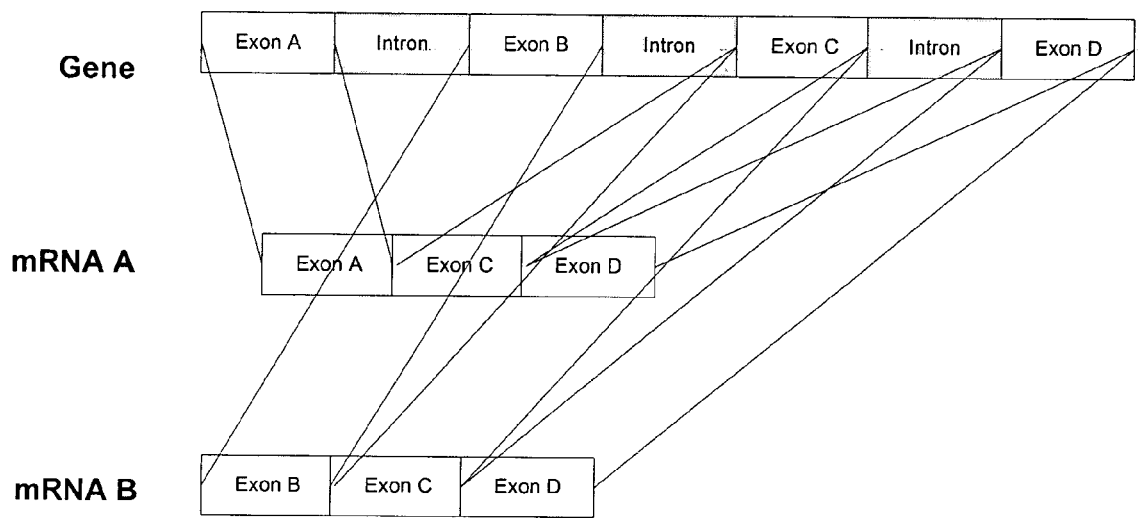
FIGURE 1: Alternative Splicing

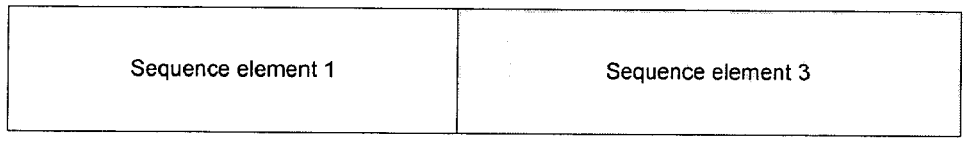
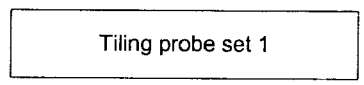
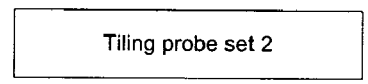
Figure 2: Detection of Combination of Sequence Elements

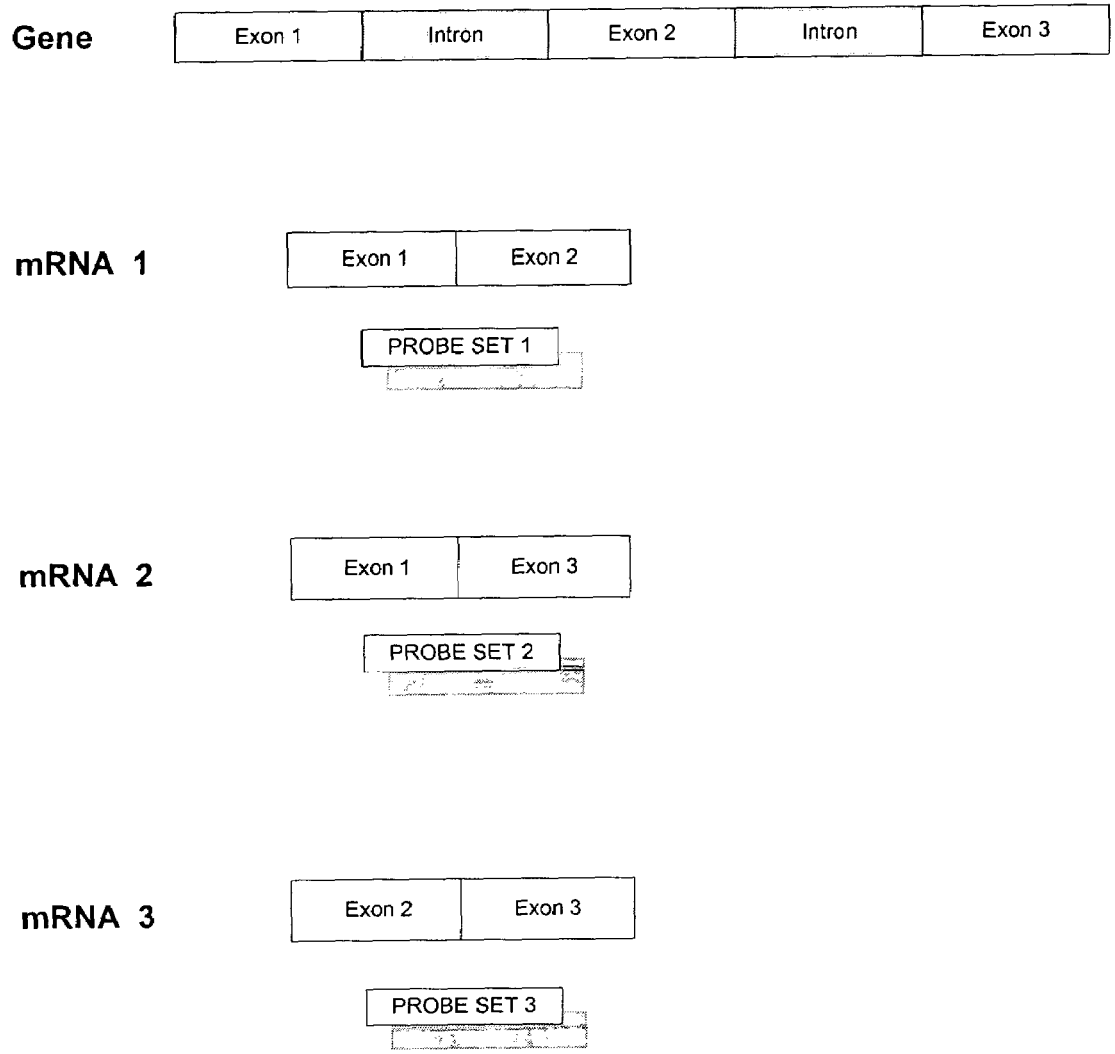
FIGURE 3: Alternative Splicing Detection Using Tiling Probe Sets

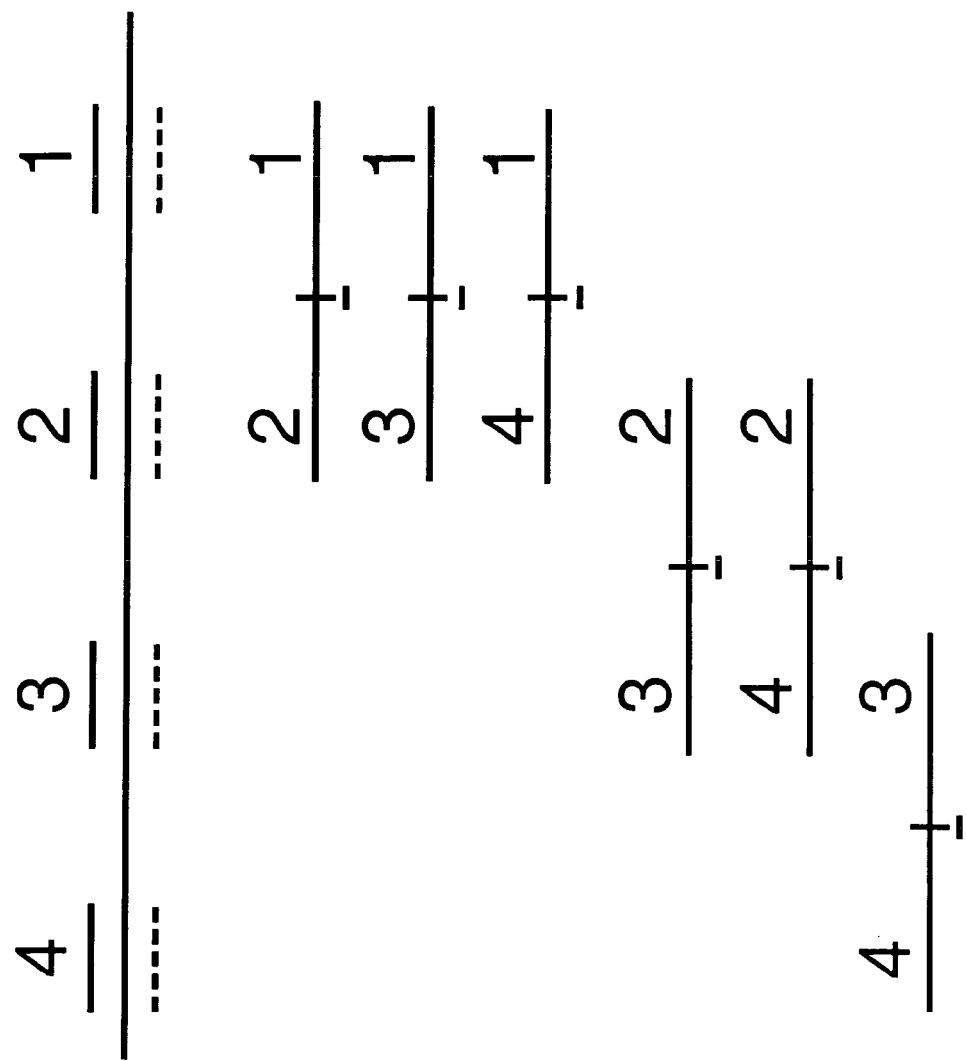

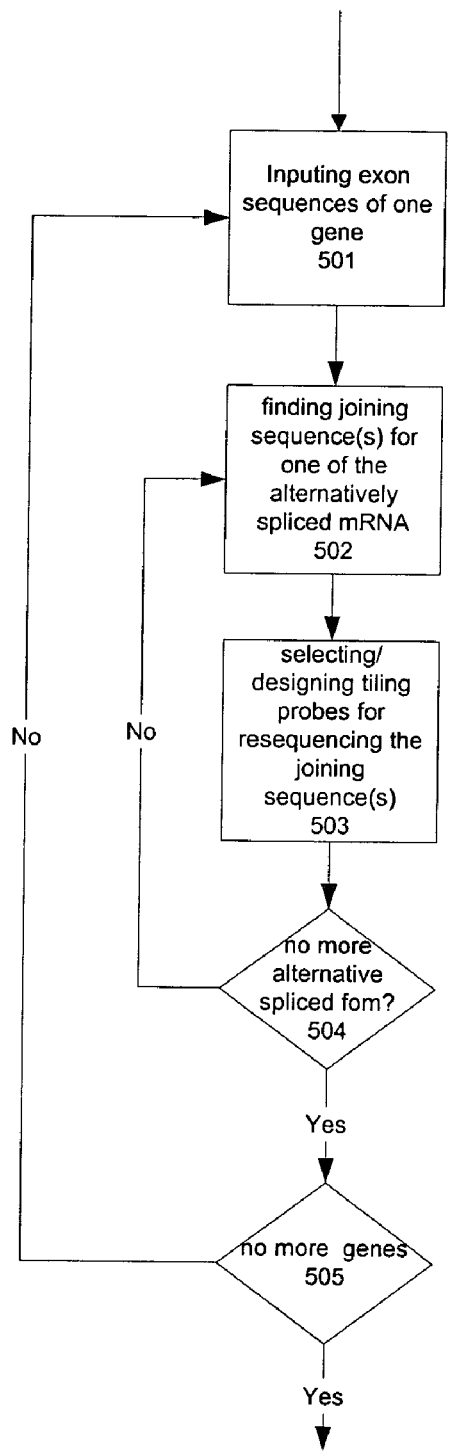
FIGURE 5: Algorithm for Designing Exon Tiling Probes

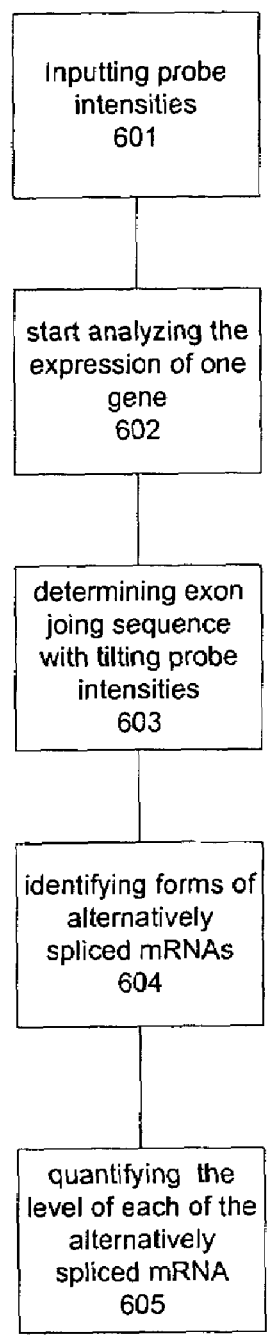
FIGURE 6: Algorithm for analyzing an exon chip

US 7,089,121 B1

METHODS FOR MONITORING THE EXPRESSION OF ALTERNATIVELY SPLICED GENES

This application is a continuation of U.S. patent application Ser. No. 10/384,275 which claims priority from U.S. Provisional Application Nos. 60/362,315, 60/362,456, 60/362,524, 60/362,454, 60/362,455, 60/362,399. This application also claims the benefit of U.S. Provisional Application Nos. 60/433,135, 60/433,225, 60/422,220, 60/398,958 and 60/384,552. All the cited applications are incorporated herein by reference for all purposes.

BACKGROUND OF THE INVENTION

U.S. Pat. Nos. 5,424,186 and 5,445,934 describe a pioneering technique for, among other things, forming and using high density arrays of molecules such as oligonucleotide, RNA, peptides, polysaccharides, and other materials. The patents are hereby incorporated by reference for all purposes. Arrays of oligonucleotides or peptides, for example, are formed on the surface by sequentially removing a photoremovable group from a surface, coupling a monomer to the exposed region of the surface, and repeating the process. These techniques have been used to form extremely dense arrays of oligonucleotides, peptides, and other materials. Such arrays are useful in, for example, drug development, gene expression monitoring, genotyping, and a variety of other applications.

The development of the nucleic acid probe array technology provides means for studying the complex regulation of expression of a large number of genes. U.S. Pat. No. 6,040,138, for example, describes the process for monitoring the expression of a large number of genes. One important aspect of gene expression regulation is the alternative splicing, a process by which different mRNAs are generated from a single gene. In some cases, the expression of a single gene can result in a large number of different mRNAs, hence, large number of different functioning proteins. For example, it has been shown that 64 different mRNA variants may be generated from a single gene. Alternative splicing is a very common regulatory mechanism. According to one estimate, at least 30% of the genes are alternatively spliced. Monitoring alternative splicing will therefore provide information for drug discovery, therapy monitoring, and diagnostics. Therefore, there is a great need in the art for methods for more efficiently determining alternatively spliced mRNA.

SUMMARY OF THE INVENTION

Accordingly, this invention provides methods, compositions, and computer software for analyzing sequence variations such as products of alternative splicing. These methods, compositions and computer software products of the invention are particularly useful for analyzing large number of alternatively spliced mRNAs. In some embodiments, methods, compositions and computer software for making and using Exon Chips are provided. The Exon Chips of the invention are particularly useful for analyzing gene regulation by alternative splicing, alternative promoters, RNA editing, etc. However, the utility of the Exon Chips are not limited to analyzing gene regulation. These chips may in general be used to analyze the arrangement of sequence elements (e.g., exons). In addition to being able to identify the specific sequence arrangements in a biological sample, the exon chip probe arrays of the invention are also useful for quantifying the specific sequences. Such probe arrays may be used to better understand the expression of genes, particularly those genes that are regulated by alternative splicing, alternative promoters, RNA editing, etc.

In one aspect of the invention, a nucleic acid probe array comprising a set of probes for interrogating the joining sequence between a first sequence element and a second sequence element is provided. In some embodiments, the probes on the probe array are oligonucleotides. The first sequence element may be a first exon and the second sequence element may be a second exon. The joining sequence is the portion of the sequence neighboring the junction between the first and second sequence. If the sequence elements are exons, the joining sequence is the 3' sequence of one exon and 5' sequence of another exon. The joining sequence should be at least 20 bases in length, preferably at least 30 bases in length, more preferably at least 40 bases in length, even more preferably at least 50 bases and most preferably 100 bases in length.

In some preferred embodiments, the set of probes are immobilized on a substrate at a density of at least 100 probes/cm$^2$, preferably at least 1000, more preferably at least 2000 probes/cm$^2$. The array may contain probes designed to quantify the sequence elements. For example, the array may contain probes targeting the internal sequence of exons. Optionally, control probes of various types may be included on the arrays of the invention.

In another aspect of the invention, a method for determining target sequence wherein said target sequence comprises a first sequence element joining a second sequence element is provided. In some embodiments, the method involves hybridizing a target sequence with a nucleic acid probe array having a set of probes for interrogating the joining sequence between a first sequence element and a second sequence element, and obtaining information about the joining sequence based upon the hybridization of the target sequence with the set of probes. The first and second sequence elements may be exons. The set of nucleic acid probes may be oligonucleotide probes immobilized on a substrate, preferably at a density of at least 100 probes/cm$^2$. In some embodiments, target sequence is a mRNA. The mRNA may be one of at least two alternatively spliced mRNAs transcribed from a gene. The method may also include the step of quantifying the first and second sequence elements using information about the joining sequence and said hybridization.

In some embodiments, the nucleic acid probe array of the invention may have additional sequence probes against the first and second sequence elements. The quantification may be based upon the hybridization of target sequence and sequence probes against the internal sequence of the first and second sequence elements. The probes for interrogating are probes for tiling the joining sequence which should be at least 20 bases in length, preferably at least 30 bases, more preferably at least 40 bases, and even more preferably at least 50 bases and most preferably at least 100 bases.

In yet another aspect of the invention, a computer software product is provided. The product may include computer code that receives a plurality of hybridization signals, wherein each of the plurality of signals reflects the hybridization of one of plurality of tiling probes to interrogate the joining sequence of a target sequence wherein the target sequence has at least one sequence element that is selected from a group of at least two sequence elements; b) Computer code that identifies the sequence element based upon said hybridization signals; and c) a computer readable media that stores said codes. The tiling probes are oligonucleotides immobilized on a substrate. The tiling probes interrogate at least 20 bases, preferably at least 30 bases, more preferably least 40 bases, even more preferably at least 50 bases and most preferably at least 100 bases. The computer software may include computer code for quantifying a target sequence.

In yet another aspect, methods for designing probes for detecting the combination of two sequence elements are provided. In some embodiments, the methods include inputting the sequence of the joining region between two sequence elements; and selecting probes for tiling the said joining region based upon the sequence of the joining region. In preferred embodiments, sequence elements are exons. In some embodiments, the method of the invention also include a step of designing lithographic mask where lithographic mask is used in the fabrication of arrays of nucleic acid probes. In some other embodiments, the method of the invention include a step of output signals for controlling an inkjet printing mechanism for depositing compounds on a substrate. The sequence of the joining region to be interrogated is at least 20 bases, preferably at least 30 bases, more preferably at least 40 bases, even more preferably at least 50 bases and most preferably at least 100 bases.

Computer software products for designing exon chips of the invention are also provided. In some embodiments, the computer software product include computer program code that constructs a joining sequence; computer program code that selects tiling probes to interrogate the joining sequence; and a computer readable media that stores said codes. The joining sequence may be for one of alternatively spliced mRNAs. In some embodiments, the computer software product also include computer code that inputs exon sequences. The joining sequence is constructed based upon the exon sequences. The computer software product may include code that outputs sequence of the probes.

BRIEF DESCRIPTION OF THE DRAWINGS

FIG. 1 shows alternative splicing.

FIG. 2 shows detection of combination of sequence elements.

FIG. 3 shows detection of alternative splicing.

FIG. 4 shows detection of more complex alternative splicing.

FIG. 5 shows the process for designing an exon chip.

FIG. 6 shows the process for analyzing data from an exon chip.

DESCRIPTION OF THE PREFERRED EMBODIMENTS

A mRNA is often the result of the combination of sequence elements. For example, a mature mRNA may be the result of RNA splicing where sequences transcribed from introns are removed. The combination of the sequence elements may be configured in alternative format. In some embodiments of the invention, methods, compositions, computer software products and systems are provided to identify the configuration (arrangement of sequence elements, such as exons) of nucleic acids. The methods, compositions, computer software products and systems are particularly useful for simultaneously quantifying and characterizing mRNAs.

I. Detecting Sequence Elements

Activity of a gene is reflected by the activity of its product(s): the proteins or other molecules encoded by the gene. Those product molecules perform biological functions. Directly measuring the activity of a gene product is, however, often difficult for certain genes. Instead, the immunological activities or the amount of the final product(s) or its peptide processing intermediates are determined as a measurement of the gene activity. More frequently, the amount or activity of intermediates, such as transcripts, RNA processing intermediates, or mature mRNAs are detected as a measurement of gene activity. The term "mRNA" refers to transcripts of a gene. Transcripts are RNAs including, for example, mature messenger RNA ready for translation, products of various stages of transcript processing. Transcript processing may include splicing, editing and degradation.

In many cases, the form and function of the final product(s) of a gene is unknown. In those cases, the activity of a gene is measured conveniently by the amount or activity of transcript(s), RNA processing intermediate(s), mature mRNA(s) or its protein product(s).

A transcriptional unit is a continuous segment of DNA that is transcribed into RNA. For example, bacteria can continuously transcribe several contiguous genes to make polycistronic mRNAs. The contiguous genes are from the same transcriptional unit. It is well known in the art that higher organisms also use several mechanisms to make a variety of different gene products from a single transcriptional unit.

Many genes are known to have several alternative promoters, the use of each promoter resulting in one particular transcript. Generally, the use of 5' promoter results in a product that has additional sequence elements that is absent in the products resulted from relatively 3' promoters. The use of alternative promoters is frequently employed to regulate tissue specific gene expression. For example, human dystrophin gene has at least seven promoters. The most 5' upstream promoter is used to transcribe a brain specific transcript; a promoter 100 kb down-stream from the first promoter is used to transcribe a muscle specific transcript and a promoter 100 kb downstream of the second promoter is used to transcribe Purkinje cell specific transcript.

Similarly, alternative splicing is also important mechanisms for regulating gene activity, frequently in a tissue specific manner. In Eukaryotes, nascent pre-mRNAs are generally not translated into proteins. Rather, they are processed in several ways to generate mature mRNAs. RNA splicing is the most common method of RNA processing. Nascent pre-mRNAs are cut and pasted by specialized apparatus called splicesomes. Some non-coding regions transcribed from the intron regions are excised. Exons are linked to form a contiguous coding region ready for translation. In some splicing reactions, a single type of nascent pre-mRNAs are used to generate multiple types of mature RNA by a process called alternative splicing in which exons (sequence elements) are alternatively used to form different mature mRNAs which code for different proteins. For example, the human Calcitonin gene (CALC) is spliced as calcitonin, a circulating $Ca^{2+}$ homeostatic hormone, in the thyroid; as calcitonin gene-related peptide (CGRP), a neuromodulatory and trophic factor, in the hypothalamus (See, Hodges and Bernstein, 1994, Adv. Genet., 31, 207–281).

Alternative splicing is an important regulatory mechanism in higher eukaryotes (Sharp, P. A. (1994) Cell., 77, 805–8152). By recent estimates, at least 30% of human genes are spliced alternatively (Mironov, A. A. and Gelfand, M. S. Proc. 1st Int. Conf. on Bioinformatics of Genome Regulation, 1998. vol. 2, p. 249). Alternative splicing plays a major role in sex determination in *Drosophila*, antibody response in humans and other tissue or developmental stage specific processes (Stamm, S., Zhang, M. Q., Marr, T. G. and Helfman, D. M., 1994, Nucleic Acids Res., 22, 1515–1526; Chabot, B., 1996, Trends Genet., 12, 472–478; Breitbart, R. E., Andreadis, A. and Nadal-Ginard, B., 1987, Annu. Rev. Biochem., 56, 467–495; Smith, C. W., Patton, J. G. and Nadal-Ginard, B., 1989, Annu. Rev. Genet., 23, 527–57). Alternative splicing can generate up to 64 different mRNA variants from a single transcript (Breitbart, R. E. and Nadal-Ginard, N. 1987, Cell, 46, 793–803). All cited references are incorporated herein by reference for all purposes.

High-density arrays are particularly useful for monitoring the expression control at the transcriptional, RNA processing and degradation level. The fabrication and application of high density arrays in gene expression monitoring have been disclosed previously in, for example, U.S. Pat. No. 6,040,138, incorporated herein by reference for all purposes. In some embodiment using high-density arrays, high-density oligonucleotide arrays are synthesized using methods such as the Very Large Scale Immobilized Polymer Synthesis (VLSIPS) disclosed in U.S. Pat. No. 5,445,934 incorporated herein for all purposes by reference. Each oligonucleotide occupies a known location on a substrate. A nucleic acid target sample is hybridized with a high-density array of oligonucleotides and then the amount of target nucleic acids hybridized to each probe in the array is quantified. One preferred quantifying method is to use confocal microscope and fluorescent labels. The GeneChip® system (Affymetrix, Santa Clara, Calif.) is particularly suitable for quantifying the hybridization; however, it is apparent to those of skill in the art that any similar systems or other effectively equivalent detection methods can also be used.

High-density arrays are suitable for quantifying small variations in expression levels of a gene in the presence of a large population of heterogeneous nucleic acids. Such high-density arrays can be fabricated either by de novo synthesis on a substrate or by spotting or transporting nature nucleic acid sequences onto specific locations of substrate. Nucleic acids are purified and/or isolated from biological materials, such as a bacteria plasmid containing a cloned segment of sequence of interest.

Oligonucleotide arrays are particularly preferred for this invention. Oligonucleotide arrays have numerous advantages, as opposed to other methods, such as efficiency of production, reduced intra- and inter array variability, increased information content and high signal to noise ratio.

Preferred high density arrays for gene function identification and genetic network mapping comprise greater than about 100, preferably greater than about 1000, more preferably greater than about 16,000 and most preferably greater than 65,000 or 250,000 or even greater than about 1,000,000 different oligonucleotide probes, preferably in less than 1 cm$^2$ of surface area. The oligonucleotide probes range from about 5 to about 50 or about 500 nucleotides, more preferably from about 10 to about 40 nucleotide and most preferably from about 15 to about 40 nucleotides in length.

Oligonucleotide probe arrays containing probes targeting exon sequences may be selected to detect and quantify various transcripts. By using these exon probes, the presence of particular exons in a biological sample may be determined. In the following sections, methods for design probe arrays for detecting and quantifying target nucleic acids of specific configurations (arrangement of sequence elements) are provided.

II. Probes for Detecting Combination of Sequence Elements

In one aspect of the invention, nucleic acid probes are provided for determining and optionally quantifying the arrangement of sequence elements. These probes may be preferably immobilized on a substrate as a probe array.

In some embodiments of the invention, a probe set is designed to interrogate the sequence of the region that joins two sequence elements (see, FIG. 2). Once the sequence of the region joining two sequence elements is known, the combination of sequence elements can be ascertained. For example, as shown in FIG. 2, two sequence elements 1 and 2 may be alternatively used to form:

Configuration 1: Element 1-element 3

Configuration 2: Element 2-element 3

Probe sets for tiling the region joining elements 1 and 3 and elements 2 and 3 may be designed to determine the presence of configurations 1 and 2. Because the hybridization signals also reflects the levels of sequences, relative levels of configuration 1 and configuration 2 in a biological sample may also be determined. Methods for quantitatively determining the level of large number of mRNAs are disclosed in, for example, U.S. Pat. No. 6,040,138, incorporated herein by reference for all purposes.

In one embodiment (FIG. 3), probes may be designed to detect the transcripts of a target gene that has three exons (from 5' to 3', exon 1, exon 2 and exon 3). In this embodiment, a first set of probes were designed for tiling the 3' region of the exon 1 and the 5' region of the exon 2. A second set of probes are designed for tiling the 3' region of the exon 1 and the 5' region of the exon 3. A third set of probes are designed for tiling the 3' region of the exon 2 and 5' region of the exon 3. The tiling region of the probe sets may be at least 10 bases, preferably at least 20 bases, and more preferably at least 40 bases. In some instances, the tiling region may be at least 100 bases.

FIG. 4 shows a gene that has four exons. Exon 1 may be spliced to join exon 2, 3 or 4. Exon 2 may be spliced to join exon 3 or 4. Exon 3 and 4 may be joined. Tiling probes (small bar under the exons) are designed to interrogate the joining sequences. Based upon the determined sequences, the various configurations may be ascertained.

Methods for designing probes for tiling a region for resequence purpose were disclosed in, for example, U.S. Pat. No. 5,571,639 and Chee et al. 1996, Accessing Genetic Information with High-Density DNA Arrays, Science, 274: 610–614, both incorporated herein by reference for all purposes.

The methods of the invention have wide applications. For example, in some embodiments, the methods of the invention may be used to determine the relative levels of splice variants. By determining the relative splice variants, the regulation of gene expression by alternative splicing may be understood, which may in turn provide information important for disease detection, drug discovery and monitoring of medical treatment.

The methods of the invention are not limited to the study of genes whose exon boundary is completely known. In contrast, because of the use of tiling probe sets, the methods of the invention allows some ambiguity of the knowledge about the exon boundary. The probe sets may be useful for understanding the precise splicing sites.

One of skill in the art would appreciate that the methods of the invention are not limited to the study of splice variants. Instead, the methods are generally applicable to the study of arrangement of any nucleic acid sequence elements. For example, the methods are also useful for determining somatic recombination and RNA editing.

III. Methods, Systems and Computer Software for Designing Probes

Methods, systems and computer software for designing the probe sets are also provided. In some embodiments, the method for designing probes include steps of obtaining sequence information of at least two sequence elements (such as two exons). The possible joining region between the two sequence elements is identified. Probes for tiling the region are selected.

In some other embodiments, genomic DNA sequence of a gene is obtained. Intron exon structure is predicted. Because of the limitation of some splicing site predication algorithms, the splice site may be somewhat ambiguously determined. Probes for tiling the joining regions between predicted exons are selected.

In some additional embodiments, the exon/intron boundary may be determined by comparing the sequence of transcripts and genomic sequences.

Probes for tiling the regions joining two exons are selected.

FIG. 5 shows a process for computer assisted selection of probes. Exon sequences of one gene are inputted (501). The joining sequence(s) for one of the alternatively spliced mRNA is constructed in a memory (502). The tiling probes to interrogate the sequence are selected (503). The process then continues to select tiling probes for another alternatively spliced mRNA (504) until all mRNA variants from the gene are processed (505). The process continues by inputting exon sequences of another gene (501).

In some embodiments, a computerized system is used for forming and analyzing arrays of biological materials such as RNA or DNA. A digital computer is used to design arrays of biological polymers such as RNA or DNA. The computer may be, for example, an appropriately programmed Sun Workstation or Intel Pentium based personal computer or work station, including appropriate memory, a CPU and other storage media such as a hard-drive, optionally a CD-ROM, a Zip drive. The computer may be connected to a network such as a local area network and connected to a wide area network, such as the Internet optionally via a proxy server. The computer's capability for accessing to the Internet may be preferred in some embodiments wherein sequence databases may be accessed via the Internet.

The computer system obtains inputs from a user regarding desired characteristics of a gene of interest, and other inputs regarding the desired features of the array. Optionally, the computer system may obtain information regarding a specific genetic sequence of interest from an external or internal database such as GenBank. The output of the computer system is a set of chip design computer files.

The chip design files are provided to a system that designs the lithographic masks used in the fabrication of arrays of molecules such as DNA. The system or process may include the hardware necessary to manufacture masks and also the necessary computer hardware and software necessary to lay the mask patterns out on the mask in an efficient manner. Such equipment may or may not be located at the same physical site. The system generates masks such as chrome-on-glass masks for use in the fabrication of polymer arrays.

The masks, as well as selected information relating to the design of the chips from a system, are used in a synthesis system. Synthesis system includes the necessary hardware and software used to fabricate arrays of polymers on a substrate or chip. For example, synthesizer includes a light source and a chemical flow cell on which the substrate or chip is placed. Mask may be placed between the light source and the substrate/chip, and the two are translated relative to each other at appropriate times for deprotection of selected regions of the chip. Selected chemical reagents are directed through flow cell for coupling to deprotected regions, as well as for washing and other operations. All operations are preferably directed by an appropriately programmed digital computer, which may or may not be the same computer as the computer(s) used in mask design and mask making.

The sequences of various probes to be synthesized on the chip are selected and the physical arrangement of the probes on the chip is determined. For example, the joining region of the target nucleic acid sequence of interest will be a k-mer, preferably k is greater than 20, more preferably more than 40 and even more preferably more than 100, while the probes on the chip will be n-mers, where n is less than k. Accordingly, it will be necessary for the software to choose and locate the n-mers that will be synthesized on the chip such that the chip may be used to determine if a particular nucleic acid sample contains the joining region of the target nucleic acid.

In general, the tiling of a sequence will be performed by taking n-base piece of the target, and determining the complement to that n-base piece. The system will then move down the target one position, and identify the complement to the next n-bit piece. These n-base pieces will be the sequences placed on the chip when only the sequence is to be tiled.

As a simple example, suppose the target nucleic acid is 5'-ACGTTGCA-3'. Suppose that the chip will have 4-mers synthesized thereon. The 4-mer probes that will be complementary to the nucleic acid of interest will be 3'-TGCA (complement to the first four positions), 3'-GCAA (complement to positions 2, 3, 4 and 5), 3'-CAAC (complement to positions 3, 4, 5 and 6), 3'-AACG (complement to positions 4, 5, 6 and 7), and 3'-ACGT (complement to the last four positions). Accordingly, assuming the user has selected sequence tiling, the system determines that the sequence of the probes to be synthesized will be 3'-TGCA, 3'-GCAA, 3'-CAAC, 3'-AACG, and 3'-ACGT. If a particular sample has the target sequence, binding will be exhibited at the sites of each 4-mer probe. If a particular sample does not have the sequence 5'-ACGTTGCA-3', little or no binding will be exhibited at the sites of one or more of the probes on the substrate.

The system then determines if additional tiling is to be done and, if so, repeats.

After the probes have been selected, the system may minimize the number of synthesis cycles need to form the array of probes. To perform this step, the probes that are to be synthesized are evaluated according to a specified algorithm to determine which bases are to be added in which order.

One algorithm uses a synthesis "template," preferably a template that allows for minimization of the number of synthesis cycles needed to form the array of probes. One "template" is the repeated addition of ACGTACGT.... All possible probes could be synthesized with a sufficiently long repetition of this template of synthesis cycles. By evaluating the probes against this (and/or other) templates, many steps may be deleted to generate various trial synthesis strategies. A trial synthesis strategy is tested by asking, for each base in the template "can the probes be synthesized without this base addition?" In other words, a "trial strategy" can be used to synthesize the probes if every base in every probe may be synthesized in the proper order using some subset of the template. If so, this base addition is deleted from the template. Other bases are then tested for removal In the specific embodiment discussed below, a synthesis strategy is developed by one or a combination of several algorithms. This methodology may be designed to result in, for example, a small number of synthesis cycles, a small number of differences between adjacent probes on the chip. In one particular embodiment, this system will reduce the number of sequence step differences between adjacent probes in "columns" of a tiled sequence, i.e., it will reduce the number of times a monomer is added in one synthesis region when it is not added in an adjacent region. These are both desirable properties of a synthesis strategy.

IV. Methods, Systems and Computer Software for Detecting Combination of Sequence Elements Methods, systems and computer software for detecting combination of sequence elements are provided. In some embodiments, a probe array is used to determine a target sequence that contains at least two sequence elements. At least one of the two sequence elements is selected from a group of at least two different sequence elements. In these embodiments, the probe array contains probes interrogating the sequence regions joining the two sequence elements. The exact arrangement of the sequence elements can be determined based upon the interrogation of the joining sequence region. In a sample containing two or more types of target sequences that have different combination of sequence arrangement (such as alternatively spliced transcripts from one gene), the relative levels of the different types of target sequences may be determined based upon hybridization intensity of interrogation probes. The term "quantifying" when used in the context of quantifying transcription levels of a gene can refer to absolute or to relative quantification. Absolute quantification may be accomplished by inclusion of known concentration(s) of one or more target nucleic acids (e.g., control nucleic acids such as Bio B or with known amounts the target nucleic acids themselves) and referencing the hybridization intensity of unknowns with the known target nucleic acids (e.g., through generation of a standard curve). Alternatively, relative quantification can be accomplished by comparison of hybridization signals between two or more genes, or between two or more treatments to quantify the changes in hybridization intensity and, by implication, transcription level. Methods for quantitatively analyzing a target sequence using single or multiple probes on a substrate is described in, for example, U.S. Pat. No. 6,040,138, incorporated herein by reference for all purposes. Levels of splice variant may be estimated using model parameters obtained through a maximum likelihood estimation process.

FIG. 6 shows a process for analyzing data from an exon chip. Probe intensities are inputted (601). The expression of one gene is being analyzed (602) using tiling probes to interrogate the genomic sequence. Tiling probes intensities are used to determine the exon joining sequence (603), identifying forms of alternatively spliced mRNAs (604). Levels of each of the alternatively spliced mRNA are quantified (605).

IV. Gene Expression Monitoring Methods

As discussed above, any methods that measure the activity of a gene are useful for at least some embodiments of this invention. For example, traditional Northern blotting and hybridization, nuclease protection, RT-PCR and differential display have been used for detecting gene activity. Those methods are useful for some embodiments of the invention. However, this invention is most useful in conjunction with methods for detecting the expression of a large number of genes.

High-density arrays are particularly useful for monitoring the expression control at the transcriptional, RNA processing and degradation level. The fabrication and application of high density arrays in gene expression monitoring have been disclosed previously in, for example, U.S. Pat. No. 5,800,992, issued Sep. 1, 1988, and U.S. application Ser. No. 08/772,376, filed Dec. 23, 1996, all incorporated herein for all purposes by reference. In some embodiments using high-density arrays, high-density oligonucleotide arrays are synthesized using methods such as the Very Large Scale Immobilized Polymer Synthesis (VLSIPS) disclosed in U.S. Pat. No. 5,445,934 incorporated herein for all purposes by reference. Each oligonucleotide occupies a known location on a substrate. A nucleic acid target sample is hybridized with a high-density array of oligonucleotides and then the amount of target nucleic acids hybridized to each probe in the array is quantified. One preferred quantifying method is to use confocal microscope and fluorescent labels. The GeneChip® Probe Array system (Affymetrix, Santa Clara, Calif.) is particularly suitable for quantifying the hybridization; however, it is apparent to those of skill in the art that any similar systems or other effectively equivalent detection methods can also be used.

High-density arrays are suitable for quantifying small variations in expression levels of a gene in the presence of a large population of heterogeneous nucleic acids. Such high-density arrays can be fabricated either by de novo synthesis on a substrate or by spotting or transporting nature nucleic acid sequences onto specific locations of substrate. Nucleic acids are purified and/or isolated from biological materials, such as a bacteria plasmid containing a cloned segment of sequence of interest. Suitable nucleic acids are also produced by amplification of templates. As a nonlimiting illustration, polymerase chain reaction, and/or in vitro transcription, are suitable nucleic acid amplification methods.

Synthesized oligonucleotide arrays are particularly preferred for this invention. Oligonucleotide arrays have numerous advantages, as opposed to other methods, such as efficiency of production, reduced intra and inter array variability, increased information content and high signal to noise ratio.

Preferred high density arrays for gene function identification and genetic network mapping comprise greater than about 100, preferably greater than about 1000, more preferably greater than about 16,000 and most preferably greater than 65,000 or 250,000 or even greater than about 1,000,000 different oligonucleotide probes, preferably in less than 1 $cm^2$ of surface area. The oligonucleotide probes range from about 5 to about 50 or about 500 nucleotides, more preferably from about 10 to about 40 nucleotide and most preferably from about 15 to about 40 nucleotides in length.

A. Massive Parallel Gene Expression Monitoring

One preferred method for massive parallel gene expression monitoring is based upon high-density nucleic acid arrays.

Generally those methods of monitoring gene expression involve (a) providing a pool of target nucleic acids comprising RNA transcript(s) of one or more target gene(s), or nucleic acids derived from the RNA transcript(s); (b) hybridizing the nucleic acid sample to a high density array of probes and (c) detecting the hybridized nucleic acids and calculating a relative and/or absolute expression (transcription, RNA processing or degradation) level.

1. Providing a Nucleic Acid Sample

One of skill in the art will appreciate that it is desirable to have nucleic samples containing target nucleic acid sequences that reflect the transcripts of interest. Therefore, suitable nucleic acid samples may contain transcripts of interest. Suitable nucleic acid samples, however, may contain nucleic acids derived from the transcripts of interest. As used herein, a nucleic acid derived from a transcript refers to a nucleic acid for whose synthesis the mRNA transcript or a subsequence thereof has ultimately served as a template. Thus, a cDNA reverse transcribed from a transcript, an RNA transcribed from that cDNA, a DNA amplified from the cDNA, an RNA transcribed from the amplified DNA, etc., are all derived from the transcript and detection of such derived products is indicative of the presence and/or abundance of the original transcript in a sample. Thus, suitable samples include, but are not limited to, transcripts of the gene or genes, cDNA reverse transcribed from the transcript, cRNA transcribed from the cDNA, DNA amplified from the genes, RNA transcribed from amplified DNA, and the like. Transcripts, as used herein, may include, but not limited to pre-mRNA nascent transcript(s), transcript processing intermediates, mature mRNA(s) and degradation products. It is not necessary to monitor all types of transcripts to practice this invention. For example, one may choose to practice the invention to measure the mature mRNA levels only.

In one embodiment, such a sample is a homogenate of cells or tissues or other biological samples. Preferably, such sample is a total RNA preparation of a biological sample. More preferably in some embodiments, such a nucleic acid sample is the total mRNA isolated from a biological sample. Those of skill in the art will appreciate that the total mRNA prepared with most methods includes not only the mature mRNA, but also the RNA processing intermediates and nascent pre-mRNA transcripts. For example, total mRNA purified with poly (T) column contains RNA molecules with poly (A) tails. Those poly A+ RNA molecules could be mature mRNA, RNA processing intermediates, nascent transcripts or degradation intermediates.

Biological samples may be of any biological tissue or fluid or cells. Frequently the sample will be a "clinical sample" which is a sample derived from a patient. Clinical samples provide a rich source of information regarding the various states of genetic network or gene expression. Some embodiments of the invention are employed to detect mutations and to identify the function of mutations. Such embodiments have extensive applications in clinical diagnostics and clinical studies. Typical clinical samples include, but are not limited to, sputum, blood, blood cells (e.g., white cells), tissue or fine needle biopsy samples, urine, peritoneal fluid, and pleural fluid, or cells therefrom. Biological samples may also include sections of tissues such as frozen sections taken for histological purposes.

Another typical source of biological samples are cell cultures where gene expression states can be manipulated to explore the relationship among genes. In one aspect of the invention, methods are provided to generate biological samples reflecting a wide variety of states of the genetic network.

One of skill in the art would appreciate that it is desirable to inhibit or destroy RNase present in homogenates before homogenates can be used for hybridization. Methods of inhibiting or destroying nucleases are well known in the art. In some preferred embodiments, cells or tissues are homogenized in the presence of chaotropic agents to inhibit nuclease. In some other embodiments, RNase are inhibited or destroyed by heart treatment followed by proteinase treatment.

Methods of isolating total mRNA are also well known to those of skill in the art. For example, methods of isolation and purification of nucleic acids are described in detail in Chapter 3 of Laboratory Techniques in Biochemistry and Molecular Biology: Hybridization With Nucleic Acid Probes, Part I. Theory and Nucleic Acid Preparation, P. Tijssen, ed. Elsevier, N.Y. (1993) and Chapter 3 of Laboratory Techniques in Biochemistry and Molecular Biology: Hybridization With Nucleic Acid Probes, Part I. Theory and Nucleic Acid Preparation, P. Tijssen, ed. Elsevier, N.Y. (1993)).

In a preferred embodiment, the total RNA is isolated from a given sample using, for example, an acid guanidinium-phenol-chloroform extraction method and polyA$^+$ mRNA is isolated by oligo dT column chromatography or by using (dT)n magnetic beads (see, e.g., Sambrook et al., Molecular Cloning: A Laboratory Manual (2nd ed.), Vols. 1–3, Cold Spring Harbor Laboratory, (1989), or Current Protocols in Molecular Biology, F. Ausubel et al., ed. Greene Publishing and Wiley-Interscience, New York (1987)).

Frequently, it is desirable to amplify the nucleic acid sample prior to hybridization. One of skill in the art will appreciate that whatever amplification method is used, if a quantitative result is desired, care must be taken to use a method that maintains or controls the relative frequencies of the amplified nucleic acids to achieve quantitative amplification.

Methods of "quantitative" amplification are well known to those of skill in the art. For example, quantitative PCR involves simultaneously co-amplifying a known quantity of a control sequence using the same primers. This provides an internal standard that may be used to calibrate the PCR reaction. The high density array may then include probes specific to the internal standard for quantification of the amplified nucleic acid.

Other suitable amplification methods include, but are not limited to polymerase chain reaction (PCR) (Innis, et al., PCR Protocols. A guide to Methods and Application. Academic Press, Inc. San Diego, (1990)), ligase chain reaction (LCR) (see Wu and Wallace, Genomics, 4: 560 (1989), Landegren, et al., Science, 241: 1077 (1988) and Barringer, et al., Gene, 89: 117 (1990), transcription amplification (Kwoh, et al., Proc. Natl. Acad. Sci. USA, 86: 1173 (1989)), and self-sustained sequence replication (Guatelli, et al., Proc. Nat. Acad. Sci. USA, 87: 1874 (1990)).

Cell lysates or tissue homogenates often contain a number of inhibitors of polymerase activity. Therefore, RT-PCR typically incorporates preliminary steps to isolate total RNA or mRNA for subsequent use as an amplification template. One tube mRNA capture method may be used to prepare poly(A)+ RNA samples suitable for immediate RT-PCR in the same tube (Boehringer Mannheim). The captured mRNA can be directly subjected to RT-PCR by adding a reverse transcription mix and, subsequently, a PCR mix.

In a particularly preferred embodiment, the sample mRNA is reverse transcribed with a reverse transcriptase and a primer consisting of oligo dT and a sequence encoding the phage T7 promoter to provide single stranded DNA template. The second DNA strand is polymerized using a DNA polymerase. After synthesis of double-stranded cDNA, T7 RNA polymerase is added and RNA is transcribed from the cDNA template. Successive rounds of transcription from each single cDNA template results in amplified RNA. Methods of in vitro polymerization are well known to those of skill in the art (see, e.g., Sambrook, supra.) and this particular method is described in detail by Van Gelder, et al., Proc. Natl. Acad. Sci. USA, 87: 1663–1667 (1990). Moreover, Eberwine et al. Proc. Natl. Acad. Sci. USA, 89: 3010–3014 provide a protocol that uses two rounds of amplification via in vitro transcription to achieve greater than $10^6$ fold amplification of the original starting material thereby permitting expression monitoring even where biological samples are limited.

CRNA amplification methods disclosed in U.S. Provisional Application No. 60/172,340, filed on Dec. 16, 1999.

It will be appreciated by one of skill in the art that the direct transcription method described above provides an antisense (aRNA) pool. Where antisense RNA is used as the target nucleic acid, the oligonucleotide probes provided in the array are chosen to be complementary to subsequences of the antisense nucleic acids. Conversely, where the target nucleic acid pool is a pool of sense nucleic acids, the oligonucleotide probes are selected to be complementary to subsequences of the sense nucleic acids. Finally, where the nucleic acid pool is double stranded, the probes may be of either sense as the target nucleic acids include both sense and antisense strands.

The protocols cited above include methods of generating pools of either sense or antisense nucleic acids. Indeed, one approach can be used to generate either sense or antisense nucleic acids as desired. For example, the cDNA can be directionally cloned into a vector (e.g., Stratagene's p Bluscript II KS (+) phagemid) such that it is flanked by the T3 and T7 promoters. In vitro transcription with the T3 polymerase will produce RNA of one sense (the sense depending on the orientation of the insert), while in vitro transcription with the T7 polymerase will produce RNA having the opposite sense. Other suitable cloning systems include phage lambda vectors designed for Cre-loxP plasmid subcloning (see e.g., Palazzolo et al., Gene, 88: 25–36 (1990)).

B. Hybridizing Nucleic Acids to High Density Array

1. Probe Design

One of skill in the art will appreciate that an enormous number of array designs are suitable for the practice of this invention. The high density array will typically include a number of probes that specifically hybridize to the sequences of interest. In addition, in a preferred embodiment, the array will include one or more control probes.

The high density array chip includes "test probes." Test probes could be oligonucleotides that range from about 5 to about 45 or 5 to about 500 nucleotides, more preferably from about 10 to about 40 nucleotides and most preferably from about 15 to about 40 nucleotides in length. In other particularly preferred embodiments the probes are 20 or 25 nucleotides in length. In another preferred embodiment, test probes are double or single strand DNA sequences. DNA sequences are isolated or cloned from nature sources or amplified from nature sources using nature nucleic acid as templates. These probes have sequences complementary to particular subsequences of the genes whose expression they are designed to detect. Thus, the test probes are capable of specifically hybridizing to the target nucleic acid they are to detect.

In addition to test probes that bind the target nucleic acid(s) of interest, the high density array can contain a number of control probes. The control probes fall into three categories referred to herein as 1) Normalization controls; 2) Expression level controls; and 3) Mismatch controls which are designed to contain at least one base that is different from that of a target sequence. Normalization controls are oligonucleotide or other nucleic acid probes that are complementary to labeled reference oligonucleotides or other nucleic acid sequences that are added to the nucleic acid sample. The signals obtained from the normalization controls after hybridization provide a control for variations in hybridization conditions, label intensity, "reading" efficiency and other factors that may cause the signal of a perfect hybridization to vary between arrays. In a preferred embodiment, signals (e.g., fluorescence intensity) read from all other probes in the array are divided by the signal (e.g., fluorescence intensity) from the control probes thereby normalizing the measurements.

Virtually any probe may serve as a normalization control. However, it is recognized that hybridization efficiency varies with base composition and probe length. Preferred normalization probes are selected to reflect the average length of the other probes present in the array, however, they can be selected to cover a range of lengths. The normalization control(s) can also be selected to reflect the (average) base composition of the other probes in the array, however in a preferred embodiment, only one or a few normalization probes are used and they are selected such that they hybridize well (i.e., no secondary structure) and do not match any target-specific probes.

Expression level controls are probes that hybridize specifically with constitutively expressed genes in the biological sample. Virtually any constitutively expressed gene provides a suitable target for expression level controls. Typically expression level control probes have sequences complementary to subsequences of constitutively expressed "housekeeping genes" including, but not limited to the βactin gene, the transferrin receptor gene, the GAPDH gene, and the like. Mismatch controls may also be provided for the probes to the target genes, for expression level controls or for normalization controls. Mismatch controls are oligonucleotide probes or other nucleic acid probes designed to be identical to their corresponding test, target or control probes except for the presence of one or more mismatched bases. A mismatched base is a base selected so that it is not complementary to the corresponding base in the target sequence to which the probe would otherwise specifically hybridize. One or more mismatches are selected such that under appropriate hybridization conditions (e.g., stringent conditions) the test or control probe would be expected to hybridize with its target sequence, but the mismatch probe would not hybridize (or would hybridize to a significantly lesser extent). Preferred mismatch probes contain a central mismatch. Thus, for example, where a probe is a 20 mer, a corresponding mismatch probe will have the identical sequence except for a single base mismatch (e.g., substituting a G, a C or a T for an A) at any of positions 6 through 14 (the central mismatch).

Mismatch probes thus provide a control for non-specific binding or cross-hybridization to a nucleic acid in the sample other than the target to which the probe is directed. Mismatch probes thus indicate whether a hybridization is specific or not. For example, if the target is present the perfect match probes should be consistently brighter than the mismatch probes. In addition, if all central mismatches are present, the mismatch probes can be used to detect a mutation. The difference in intensity between the perfect match and the mismatch probe (I(PM)-I(MM)) provides a good measure of the concentration of the hybridized material.

The high density array may also include sample preparation/amplification control probes. These are probes that are complementary to subsequences of control genes selected because they do not normally occur in the nucleic acids of the particular biological sample being assayed. Suitable sample preparation/amplification control probes include, for example, probes to bacterial genes (e.g., Bio B) where the sample in question is a biological from a eukaryote.

The RNA sample is then spiked with a known amount of the nucleic acid to which the sample preparation/amplification control probe is directed before processing. Quantification of the hybridization of the sample preparation/amplification control probe then provides a measure of alteration in the abundance of the nucleic acids caused by processing steps (e.g., PCR, reverse transcription, in vitro transcription, etc.).

In a preferred embodiment, oligonucleotide probes in the high density array are selected to bind specifically to the nucleic acid target to which they are directed with minimal non-specific binding or cross-hybridization under the particular hybridization conditions utilized. Because the high density arrays of this invention can contain in excess of 1,000,000 different probes, it is possible to provide every probe of a characteristic length that binds to a particular nucleic acid sequence. Thus, for example, the high density array can contain every possible 20 mer sequence complementary to an IL-2 mRNA.

There, however, may exist 20 mer subsequences that are not unique to the IL-2 mRNA. Probes directed to these subsequences are expected to cross hybridize with occurrences of their complementary sequence in other regions of the sample genome. Similarly, other probes simply may not hybridize effectively under the hybridization conditions (e.g., due to secondary structure, or interactions with the substrate or other probes). Thus, in a preferred embodiment, the probes that show such poor specificity or hybridization efficiency are identified and may not be included either in the high density array itself (e.g., during fabrication of the array) or in the post-hybridization data analysis.

In addition, in a preferred embodiment, expression monitoring arrays are used to identify the presence and expression (transcription) level of genes which are several hundred base pairs long. For most applications it would be useful to identify the presence, absence, or expression level of several thousand to one hundred thousand genes. Because the number of oligonucleotides per array is limited in a preferred embodiment, it is desired to include only a limited set of probes specific to each gene whose expression is to be detected.

As disclosed in U.S. application Ser. No. 08/772,376, probes as short as 15, 20, or 25 nucleotide are sufficient to hybridize to a subsequence of a gene and that, for most genes, there is a set of probes that performs well across a wide range of target nucleic acid concentrations. In a preferred embodiment, it is desirable to choose a preferred or "optimum" subset of probes for each gene before synthesizing the high density array.

2. Forming High Density Arrays.

Methods of forming high density arrays of oligonucleotides, peptides and other polymer sequences with a minimal number of synthetic steps are known. The oligonucleotide analogue array can be synthesized on a solid substrate by a variety of methods, including, but not limited to, light-directed chemical coupling, and mechanically directed coupling. See Pirrung et al., U.S. Pat. No. 5,143,854 (see also PCT Application No. WO 90/15070) and Fodor et al., PCT Publication Nos. WO 92/10092 and WO 93/09668 and U.S. Ser. No. 07/980,523 which disclose methods of forming vast arrays of peptides, oligonucleotides and other molecules using, for example, light-directed synthesis techniques. See also, Fodor et al., Science, 251, 767–77 (1991). These procedures for synthesis of polymer arrays are now referred to as VLSIPS™ procedures. Using the VLSIPS™ approach, one heterogeneous array of polymers is converted, through simultaneous coupling at a number of reaction sites, into a different heterogeneous array. See, U.S. application Ser. Nos. 07/796,243 and 07/980,523.

The development of VLSIPS™ technology as described in the above-noted U.S. Pat. No. 5,143,854 and PCT patent publication Nos. WO 90/15070 and 92/10092, is considered pioneering technology in the fields of combinatorial synthesis and screening of combinatorial libraries. More recently, patent application Ser. No. 08/082,937, filed Jun. 25, 1993 describes methods for making arrays of oligonucleotide probes that can be used to check or determine a partial or complete sequence of a target nucleic acid and to detect the presence of a nucleic acid containing a specific oligonucleotide sequence.

In brief, the light-directed combinatorial synthesis of oligonucleotide arrays on a glass surface proceeds using automated phosphoramidite chemistry and chip masking techniques. In one specific implementation, a glass surface is derivatized with a silane reagent containing a functional group, e.g., a hydroxyl or amine group blocked by a photolabile protecting group. Photolysis through a photolithogaphic mask is used selectively to expose functional groups which are then ready to react with incoming 5'-photoprotected nucleoside phosphoramidites. The phosphoramidites react only with those sites which are illuminated (and thus exposed by removal of the photolabile blocking group). Thus, the phosphoramidites only add to those areas selectively exposed from the preceding step. These steps are repeated until the desired array of sequences have been synthesized on the solid surface. Combinatorial synthesis of different oligonucleotide analogues at different locations on the array is determined by the pattern of illumination during synthesis and the order of addition of coupling reagents.

In the event that an oligonucleotide analogue with a polyamide backbone is used in the VLSIPS™ procedure, it is generally inappropriate to use phosphoramidite chemistry to perform the synthetic steps, since the monomers do not attach to one another via a phosphate linkage. Instead, peptide synthetic methods are substituted. See, e.g., Pirrung et al. U.S. Pat. No. 5,143,854.

Peptide nucleic acids are commercially available from, e.g., Biosearch, Inc. (Bedford, Mass.) which comprise a polyamide backbone and the bases found in naturally occurring nucleosides. Peptide nucleic acids are capable of binding to nucleic acids with high specificity, and are considered "oligonucleotide analogues" for purposes of this disclosure. In addition to the foregoing, additional methods which can be used to generate an array of oligonucleotides on a single substrate are described in co-pending application Ser. No. 07/980,523, filed Nov. 20, 1992, and 07/796,243, filed Nov. 22, 1991 and in PCT Publication No. WO 93/09668. In the methods disclosed in these applications, reagents are delivered to the substrate by either (1) flowing within a channel defined on predefined regions or (2) "spotting" on predefined regions or (3) through the use of photoresist. However, other approaches, as well as combinations of spotting and flowing, may be employed. In each instance, certain activated regions of the substrate are mechanically separated from other regions when the monomer solutions are delivered to the various reaction sites.

A typical "flow channel" method applied to the compounds and libraries of the present invention can generally be described as follows. Diverse polymer sequences are synthesized at selected regions of a substrate or solid support by forming flow channels on a surface of the substrate through which appropriate reagents flow or in which appropriate reagents are placed. For example, assume a monomer "A" is to be bound to the substrate in a first group of selected regions. If necessary, all or part of the surface of the substrate in all or a part of the selected regions is activated for binding by, for example, flowing appropriate reagents through all or some of the channels, or by washing the entire substrate with appropriate reagents. After placement of a channel block on the surface of the substrate, a reagent having the monomer A flows through or is placed in all or some of the channel(s). The channels provide fluid contact to the first selected regions, thereby binding the monomer A on the substrate directly or indirectly (via a spacer) in the first selected regions.

Thereafter, a monomer B is coupled to second selected regions, some of which may be included among the first selected regions. The second selected regions will be in fluid contact with a second flow channel(s) through translation, rotation, or replacement of the channel block on the surface of the substrate; through opening or closing a selected valve; or through deposition of a layer of chemical or photoresist. If necessary, a step is performed for activating at least the second regions. Thereafter, the monomer B is flowed through or placed in the second flow channel(s), binding monomer B at the second selected locations. In this particular example, the resulting sequences bound to the substrate at this stage of processing will be, for example, A, B, and AB. The process is repeated to form a vast array of sequences of desired length at known locations on the substrate.

After the substrate is activated, monomer A can be flowed through some of the channels, monomer B can be flowed through other channels, a monomer C can be flowed through still other channels, etc. In this manner, many or all of the reaction regions are reacted with a monomer before the channel block must be moved or the substrate must be washed and/or reactivated. By making use of many or all of the available reaction regions simultaneously, the number of washing and activation steps can be minimized.

One of skill in the art will recognize that there are alternative methods of forming channels or otherwise protecting a portion of the surface of the substrate. For example, according to some embodiments, a protective coating such as a hydrophilic or hydrophobic coating (depending upon the nature of the solvent) is utilized over portions of the substrate to be protected, sometimes in combination with materials that facilitate wetting by the reactant solution in other regions. In this manner, the flowing solutions are further prevented from passing outside of their designated flow paths.

High density nucleic acid arrays can be fabricated by depositing presynthezied or nature nucleic acids in predined positions. As disclosed in the U.S. Application Ser. No. and its parent applications, previously incorporated for all purposed, synthesized or nature nucleic acids are deposited on specific locations of a substrate by light directed targeting and oligonucleotide directed targeting. Nucleic acids can also be directed to specific locations in much the same manner as the flow channel methods. For example, a nucleic acid A can be delivered to and coupled with a first group of reaction regions which have been appropriately activated. Thereafter, a nucleic acid B can be delivered to and reacted with a second group of activated reaction regions. Nucleic acids are deposited in selected regions. Another embodiment uses a dispenser that moves from region to region to deposit nucleic acids in specific spots. Typical dispensers include a micropipette or capillary pin to deliver nucleic acid to the substrate and a robotic system to control the position of the micropipette with respect to the substrate. In other embodiments, the dispenser includes a series of tubes, a manifold, an array of pipettes or capillary pins, or the like so that various reagents can be delivered to the reaction regions simultaneously.

3. Hybridization

Nucleic acid hybridization simply involves contacting a probe and target nucleic acid under conditions where the probe and its complementary target can form stable hybrid duplexes through complementary base pairing. The nucleic acids that do not form hybrid duplexes are then washed away leaving the hybridized nucleic acids to be detected, typically through detection of an attached detectable label. It is generally recognized that nucleic acids are denatured by increasing the temperature or decreasing the salt concentration of the buffer containing the nucleic acids. Under low stringency conditions (e.g., low temperature and/or high salt) hybrid duplexes (e.g., DNA:DNA, RNA:RNA, or RNA:DNA) will form even where the annealed sequences are not perfectly complementary. Thus specificity of hybridization is reduced at lower stringency. Conversely, at higher stringency (e.g., higher temperature or lower salt) successful hybridization requires fewer mismatches.

One of skill in the art will appreciate that hybridization conditions may be selected to provide any degree of stringency. In a preferred embodiment, hybridization is performed at low stringency in this case in 6×SSPE-T at 37 C (0.005% Triton X-100) to ensure hybridization and then subsequent washes are performed at higher stringency (e.g., 1 ×SSPE-T at 37 C) to eliminate mismatched hybrid duplexes. Successive washes may be performed at increasingly higher stringency (e.g., down to as low as 0.25× SSPE-T at 37 C to 50 C) until a desired level of hybridization specificity is obtained. Stringency can also be increased by the addition of agents such as formamide. Hybridization specificity may be evaluated by comparison of hybridization to the test probes with hybridization to the various controls that can be present (e.g., expression level control, normalization control, mismatch controls, etc.). In general, there is a tradeoff between hybridization specificity (stringency) and signal intensity. Thus, in a preferred embodiment, the wash is performed at the highest stringency that produces consistent results and that provides a signal intensity greater than approximately 10% of the background intensity. Thus, in a preferred embodiment, the hybridized array may be washed at successively higher stringency solutions and read between each wash. Analysis of the data sets thus produced will reveal a wash stringency above which the hybridization pattern is not appreciably altered and which provides adequate signal for the particular oligonucleotide probes of interest.

In a preferred embodiment, background signal is reduced by the use of a detergent (e.g., C-TAB) or a blocking reagent (e.g., sperm DNA, cot-1 DNA, etc.) during the hybridization to reduce non-specific binding. In a particularly preferred embodiment, the hybridization is performed in the presence of about 0.5 mg/ml DNA (e.g., herring sperm DNA). The use of blocking agents in hybridization is well known to those of skill in the art (see, e.g., Chapter 8 in P. Tijssen, supra.)

The stability of duplexes formed between RNAs or DNAs are generally in the order of RNA:RNA>RNA:DNA>DNA:DNA, in solution. Long probes have better duplex stability with a target, but poorer mismatch discrimination than shorter probes (mismatch discrimination refers to the measured hybridization signal ratio between a perfect match probe and a single base mismatch probe). Shorter probes (e.g., 8-mers) discriminate mismatches very well, but the overall duplex stability is low.

Altering the thermal stability ($T_m$) of the duplex formed between the target and the probe using, e.g., known oligonucleotide analogues allows for optimization of duplex stability and mismatch discrimination. One useful aspect of altering the $T_m$ arises from the fact that adenine-thymine (A-T) duplexes have a lower $T_m$ than guanine-cytosine (G-C) duplexes, due in part to the fact that the A-T duplexes have 2 hydrogen bonds per base-pair, while the G-C duplexes have 3 hydrogen bonds per base pair. In heterogeneous oligonucleotide arrays in which there is a non-uniform distribution of bases, it is not generally possible to optimize hybridization for each oligonucleotide probe simultaneously. Thus, in some embodiments, it is desirable to selectively destabilize G-C duplexes and/or to increase the stability of A-T duplexes. This can be accomplished, e.g., by substituting guanine residues in the probes of an array which form G-C duplexes with hypoxanthine, or by substituting adenine residues in probes which form A-T duplexes with 2,6 diaminopurine or by using the salt tetramethyl ammonium chloride (TMACl) in place of NaCl.

Altered duplex stability conferred by using oligonucleotide analogue probes can be ascertained by following, e.g., fluorescence signal intensity of oligonucleotide analogue arrays hybridized with a target oligonucleotide over time. The data allow optimization of specific hybridization conditions at, e.g., room temperature (for simplified diagnostic applications in the future).

Another way of verifying altered duplex stability is by following the signal intensity generated upon hybridization with time. Previous experiments using DNA targets and DNA chips have shown that signal intensity increases with time, and that the more stable duplexes generate higher signal intensities faster than less stable duplexes. The signals reach a plateau or "saturate" after a certain amount of time due to all of the binding sites becoming occupied. These data allow for optimization of hybridization, and determination of the best conditions at a specified temperature.

Methods of optimizing hybridization conditions are well known to those of skill in the art (see, e.g., Laboratory Techniques in Biochemistry and Molecular Biology, Vol. 24: Hybridization With Nucleic Acid Probes, P. Tijssen, ed. Elsevier, N.Y., (1993)).

C. Signal Detection

In a preferred embodiment, the hybridized nucleic acids are detected by detecting one or more labels attached to the sample nucleic acids. The labels may be incorporated by any of a number of means well known to those of skill in the art. However, in a preferred embodiment, the label is simultaneously incorporated during the amplification step in the preparation of the sample nucleic acids. Thus, for example, polymerase chain reaction (PCR) with labeled primers or labeled nucleotides will provide a labeled amplification product. In a preferred embodiment, transcription amplification, as described above, using a labeled nucleotide (e.g., fluorescein-labeled UTP and/or CTP) incorporates a label into the transcribed nucleic acids.

Alternatively, a label may be added directly to the original nucleic acid sample (e.g., mRNA, polyA mRNA, cDNA, etc.) or to the amplification product after the amplification is completed. Means of attaching labels to nucleic acids are well known to those of skill in the art and include, for example nick translation or end-labeling (e.g., with a labeled RNA) by kinasing of the nucleic acid and subsequent attachment (ligation) of a nucleic acid linker joining the sample nucleic acid to a label (e.g., a fluorophore).

Detectable labels suitable for use in the present invention include any composition detectable by spectroscopic, photochemical, biochemical, immunochemical, electrical, optical or chemical means. Useful labels in the present invention include biotin for staining with labeled streptavidin conjugate, magnetic beads (e.g., Dynabeads™), fluorescent dyes (e.g., fluorescein, texas red, rhodamine, green fluorescent protein, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and calorimetric labels such as colloidal gold or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241.

Means of detecting such labels are well known to those of skill in the art. Thus, for example, radiolabels may be detected using photographic film or scintillation counters, fluorescent markers may be detected using a photodetector to detect emitted light. Enzymatic labels are typically detected by providing the enzyme with a substrate and detecting the reaction product produced by the action of the enzyme on the substrate, and colorimetric labels are detected by simply visualizing the colored label. One particularly preferred method uses colloidal gold label that can be detected by measuring scattered light.

The label may be added to the target (sample) nucleic acid(s) prior to, or after the hybridization. So called "direct labels" are detectable labels that are directly attached to or incorporated into the target (sample) nucleic acid prior to hybridization. In contrast, so called "indirect labels" are joined to the hybrid duplex after hybridization. Often, the indirect label is attached to a binding moiety that has been attached to the target nucleic acid prior to the hybridization. Thus, for example, the target nucleic acid may be biotinylated before the hybridization. After hybridization, an aviden-conjugated fluorophore will bind the biotin bearing hybrid duplexes providing a label that is easily detected. For a detailed review of methods of labeling nucleic acids and detecting labeled hybridized nucleic acids see Laboratory Techniques in Biochemistry and Molecular Biology, Vol. 24: Hybridization With Nucleic Acid Probes, P. Tijssen, ed. Elsevier, N.Y., (1993)).

Fluorescent labels are preferred and easily added during an in vitro transcription reaction. In a preferred embodiment, fluorescein labeled UTP and CTP are incorporated into the RNA produced in an in vitro transcription reaction as described above.

Means of detecting labeled target (sample) nucleic acids hybridized to the probes of the high density array are known to those of skill in the art. Thus, for example, where a calorimetric label is used, simple visualization of the label is sufficient. Where a radioactive labeled probe is used, detection of the radiation (e.g., with photographic film or a solid state detector) is sufficient.

In a preferred embodiment, however, the target nucleic acids are labeled with a fluorescent label and the localization of the label on the probe array is accomplished with fluorescent microscopy. The hybridized array is excited with a light source at the excitation wavelength of the particular fluorescent label and the resulting fluorescence at the emission wavelength is detected. In a particularly preferred embodiment, the excitation light source is a laser appropriate for the excitation of the fluorescent label.

The confocal microscope may be automated with a computer-controlled stage to automatically scan the entire high density array. Similarly, the microscope may be equipped with a phototransducer (e.g., a photomultiplier, a solid state array, a CCD camera, etc.) attached to an automated data acquisition system to automatically record the fluorescence signal produced by hybridization to each oligonucleotide probe on the array. Such automated systems are described at length in U.S. Pat. No. 5,143,854, PCT Application 92/10092, and copending U.S. application Ser. No. 08/195,889 filed on Feb. 10, 1994. Use of laser illumination in conjunction with automated confocal microscopy for signal detection permits detection at a resolution of better than about 100 µm, more preferably better than about 50 µm, and most preferably better than about 25 µm.

One of skill in the art will appreciate that methods for evaluating the hybridization results vary with the nature of the specific probe nucleic acids used as well as the controls provided. In the simplest embodiment, simple quantification of the fluorescence intensity for each probe is determined. This is accomplished simply by measuring probe signal strength at each location (representing a different probe) on the high density array (e.g., where the label is a fluorescent label, detection of the amount of florescence (intensity) produced by a fixed excitation illumination at each location on the array). Comparison of the absolute intensities of an array hybridized to nucleic acids from a "test" sample with intensities produced by a "control" sample provides a measure of the relative expression of the nucleic acids that hybridize to each of the probes.

One of skill in the art, however, will appreciate that hybridization signals will vary in strength with efficiency of hybridization, the amount of label on the sample nucleic acid and the amount of the particular nucleic acid in the sample. Typically nucleic acids present at very low levels (e.g., <1 pM) will show a very weak signal. At some low level of concentration, the signal becomes virtually indistinguishable from the background. In evaluating the hybridization data, a threshold intensity value may be selected below which a signal is not counted as being essentially indistinguishable from background.

D. Additional Embodiments

In one embodiment of the invention, transcripts (preferably at least 100, 1000, 10000 or all known transcripts) are identified based on sequence databases including public sequence databases. These sequences are then aligned to genomic sequence such as the golden path genomic sequence using, for example, Pslayout. Gene features are then identified based on the alignment. These features include exon, partial exon, intron, exon—exon junction, exon-intron and intron-exon junction sequences. Probes (typically oligonucleotide of at least 20, 25, 30, 40, 50, 60 bases) for detecting each of these features are then selected.

The probes can be spotted or synthesized in situ to form microarrays for detecting alternatively spliced transcripts.

The above description is illustrative and not restrictive. Many variations of the invention will become apparent to those of skill in the art upon review of this disclosure. The scope of the invention should, therefore, be determined not with reference to the above description, but instead should be determined with reference to the appended claims along with their full scope of equivalents.

We claim:

1. A computer-implemented method for analyzing the expression of splice variants comprising:
   a. Selecting a plurality of transcripts of a gene from sequence databases;
   b. Aligning a sequence of said transcripts to a corresponding genomic sequence;
   c. Identifying gene features from at least one part of said transcripts aligned with the corresponding genomic sequence;
   d. Selecting oligonucleotides probes targeting said gene features;
   e. Hybridizing a target nucleic acid to an array of said oligonucleotide probes;
   f. Obtaining a plurality of probe intensities, wherein the probe intensities indicates the level of the hybridization of nucleic acid probes with various gene structures wherein the structures identify each splice variant;
   g. Analyzing the probe intensities across multiple experiments with a model-based algorithm wherein the gene structures are constraints; and
   h. Estimating the relative concentration of the splice variants with model parameters wherein the model parameters are obtained through a maximum likelihood estimation process.

2. The method of claim 1 wherein the oligonucleotide probes are immobilized on a substrate.

3. The method of claim 1 wherein the gene features include a plurality of exons.

4. The method of claim 1 wherein the gene features include at least one partial exon.

5. The method of claim 1 wherein the gene features include at least one intron.

6. The method of claim 1 wherein the gene features include at least one exon—exon junction, one exon-intron junction and one intron-exon junction.

7. The method of claim 1 wherein a combination of the gene features defines a splice variant.

* * * * *